(12) United States Patent
Nijsen et al.

(10) Patent No.: US 11,016,066 B2
(45) Date of Patent: May 25, 2021

(54) COMPACT GAS ANALYSIS DEVICE AND METHOD

(71) Applicant: KONINKLIJKE PHILIPS N.V., Eindhoven (NL)

(72) Inventors: Tamara Mathea Elisabeth Nijsen, Wert (NL); Johannes Weda, Nijmegen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 155 days.

(21) Appl. No.: 16/310,469

(22) PCT Filed: Jun. 12, 2017

(86) PCT No.: PCT/EP2017/064210
§ 371 (c)(1),
(2) Date: Dec. 17, 2018

(87) PCT Pub. No.: WO2017/216079
PCT Pub. Date: Dec. 21, 2017

(65) Prior Publication Data
US 2019/0331660 A1   Oct. 31, 2019

Related U.S. Application Data

(66) Substitute for application No. 62/351,342, filed on Jun. 17, 2016.

(51) Int. Cl.
*G01N 30/60* (2006.01)
*G01N 30/46* (2006.01)
(Continued)

(52) U.S. Cl.
CPC ....... *G01N 30/6039* (2013.01); *G01N 30/461* (2013.01); *G01N 30/463* (2013.01);
(Continued)

(58) Field of Classification Search
CPC .. G01N 30/461; G01N 30/466; G01N 30/468; G01N 30/463; G01N 30/465;
(Continued)

(56) References Cited

U.S. PATENT DOCUMENTS 9,921,192 B2 * 3/2018 Chou ................... G01N 30/463
2002/0148353 A1 * 10/2002 Seeley ................. G01N 30/463
95/86
(Continued)

FOREIGN PATENT DOCUMENTS

AU   2013205139 B2   5/2013
RU   2054669         2/1996
WO   2015124468 A1   8/2015

OTHER PUBLICATIONS

Dragonieri et al: "An Electronic Nose in the Discrimination of Patients With Asthma and Controls"; American Academy of Allergy, Asthma & Immunology; 2007, pp. 856-862.
(Continued)

*Primary Examiner* — Paul M. West

(57) ABSTRACT

A gas analysis device suited for e.g. medical analysis of exhaled breath from a subject. A gas inlet receives a gas sample to a flow path for guiding the gas sample to two or more gas separators, e.g. gas chromatography columns, with respective molecule selectivity properties which are different. One or more detectors, each with a sensor, are arranged to generate respective responses to outputs from the two or more gas separators. A communication module generate output data in response to the respective responses from the one or more detectors, e.g. data indicative of selected molecules in the gas sample, e.g. data indicative of one or more diseases identified as a result of identified biomarkers in the gas sample. The device is suitable as a compact device, e.g. a handheld breath analysis device, since the use of a plurality of gas separators allows use of very molecule
(Continued)

specific gas separators which can be implemented with a small size. E.g. a flow path with several parallel paths each comprising one or more gas separator may be used.

14 Claims, 3 Drawing Sheets

(51) Int. Cl.
*G01N 30/78* (2006.01)
*G01N 33/497* (2006.01)
*G01N 30/00* (2006.01)
*G01N 30/02* (2006.01)
*G01N 30/88* (2006.01)
*G01N 30/62* (2006.01)

(52) U.S. Cl.
CPC ......... *G01N 30/465* (2013.01); *G01N 30/468* (2013.01); *G01N 30/78* (2013.01); *G01N 33/497* (2013.01); *G01N 30/466* (2013.01); *G01N 30/6043* (2013.01); *G01N 2030/0095* (2013.01); *G01N 2030/025* (2013.01); *G01N 2030/628* (2013.01); *G01N 2030/884* (2013.01); *G01N 2030/8813* (2013.01); *G01N 2033/4975* (2013.01)

(58) Field of Classification Search
CPC ......... G01N 2030/628; G01N 30/6039; G01N 30/6043; G01N 33/497
See application file for complete search history.

(56) References Cited

U.S. PATENT DOCUMENTS

| | | |
|---|---|---|
| 2003/0027354 A1 | 2/2003 | Geli |
| 2003/0006072 A1 | 3/2003 | Lin et al. |
| 2005/0063865 A1 | 3/2005 | Bonne et al. |
| 2009/0308136 A1 | 12/2009 | Wang et al. |
| 2011/0005300 A1 | 1/2011 | Wang et al. |
| 2011/0021942 A1 | 1/2011 | Choe et al. |
| 2011/0023581 A1 | 2/2011 | Chou et al. |
| 2012/0309048 A1 | 12/2012 | Ratcliffe et al. |
| 2013/0160520 A1 | 6/2013 | Lawata et al. |
| 2014/0298990 A1* | 10/2014 | Fan .............. G01N 30/465 95/23 |
| 2015/0126887 A1 | 5/2015 | Mason et al. |

OTHER PUBLICATIONS

Fens et al: "Exhaled Breath Profiling Enables Discrimination of Chronic Obstructive Pulmonary Disease and Asthma"; Am J Respir Cri Care Med, vol. 180, pp. 1076-1082, 2009.

Montuschi et al: "Diagnostic Performance of an Electronic Nose, Fractional Exhaled Nitric Oxide, and Lung Function Testing in Asthma"; Chest 2010, 137(4): 790-796.

Peng et al: "Diagnosing Lung Cancer in Exhaled Breath Using Gold Nanoparticles"; Nature Nanotechnology, vol. 4, Oct. 2009, pp. 669-673.

Phillips et al: "Breath Biomarkers of Active Pulmonary Tuberculosis"; Tuberculosis 90 (2010), pp. 145-151.

Qin et al: "iGC1: and Integrated Fluidic System for Gas Chromatography Including Knudsen Pump, Preconentrator, Column, and Detector Microfacricated by a Three-Mask Process"; IEEE Journal of Microelectromechanical Systems, vol. 23, No. 4, Aug. 2014, pp. 980-990.

Westhoff et al: "Ion Mobility Spectrometry for the Detection of Volatile Organic Compounds in Exhaled Breath of Patients With Lung Cancer: Results of a Pilot Study"; Thorax 2009, 64:744-748.

* cited by examiner

COMPACT GAS ANALYSIS DEVICE AND METHOD

CROSS-REFERENCE TO PRIOR APPLICATIONS

This application is the U.S. National Phase application under 35 U.S.C. § 371 of International Application No. PCT/EP2017/064210, filed on Jun. 12, 2017, which claims the benefit of U.S. Provisional Patent Application No. 62/351,342, filed on Jun. 17, 2016. These applications are hereby incorporated by reference herein.

FIELD OF THE INVENTION

The invention relates generally to analysis of gas. Specifically, the invention relates to a method and a device suited for medical analysis of gas, e.g. breath exhaled from a person or gas based on samples from skin, urine or feces.

BACKGROUND OF THE INVENTION

Exhaled breath analysis in health and disease is an area of growing clinical interest. Using breath as a biological sample is appealing, because breath-collection is cheap, easy to perform and non-invasive. Volatile Organic Compounds (VOCs) are excreted from the skin, urine, feces and most notably via exhaled breath. Besides pulmonary origin, VOCs also originate from the blood, reflecting any physiological, pathological or pathogen related biochemical processes throughout the body. As such exhaled breath analysis may allow metabolic fingerprinting of disease processes anywhere inside the body.

Several studies have shown the diagnostic potential of these techniques in clearly defined subsets of patients with various diseases. The volatiles in exhaled breath change when an illness is present, and specific markers can be linked to specific diseases. The detection of these specific markers in very low amount in a complex matrix of other volatile compounds present in exhaled breath, is a challenge for even the state of the art analysis techniques.

Prior art methods typically include a separation and a detector step, if necessary with a pre-concentrator in order to increase the concentration.

The current state of the art in breath analysis are so-called electronic noses on the one hand, and gas chromatography-mass spectrometry (GC-MS) systems at the other hand. Electronic noses comprise an array of different detectors that react differently to a given type of compound. The combination of signals from the array can be used as a kind of fingerprinting method to identify the type of compound. Sensitivity and selectivity of these detectors are not suited for identifying a specific marker in the complex exhaled breath matrix.

On the other hand, high end GC-MS systems used for this purpose comprise a chromatographic column that separate the individual compounds of the matrix, and a mass spectrometry detector that can accurately detect each compound that is separated, giving the selectivity and specificity that is needed. These GC-MS systems are very expensive and bulky, and require highly skilled technicians to operate, as well as regular calibration and cleaning. Thus, such high-end equipment is not suited for use e.g. in a hospital close to the patients.

SUMMARY OF THE INVENTION

Following the above, the inventors of the present invention have appreciated that an improved device and method for gas-analysis is advantageous. Specifically, such method and device preferably allows analysis of exhaled breath from a breathing person or animal with a small device, e.g. a handheld device, and still with a specificity to allow identification or diagnosis of one or more selected diseases.

In particular, it may be seen as an object of the present invention to provide a device and method that solves the above mentioned problems, or other problems, of the prior art.

In a first aspect, the invention provides a gas analysis device comprising a gas inlet arranged to receive a gas sample, a flow path connected to the gas inlet and being arranged to guide the gas sample to at least first and second gas separators with respective first and second molecule selectivity properties, wherein the first and second molecule selectivity properties are different, at least one detector comprising a sensor arranged to generate respective first and second responses to outputs from the first and second gas separators, and a communication module arranged to generate output data in response to the first and second responses from the at least one detector.

Such gas analysis device is advantageous, since the inventors have realized that the use of a plurality of gas separators arranged in the flow path, which is split in serial and/or parallel paths, allows the use of miniature gas separators, e.g. miniature GS columns, each tuned with different molecule selectivity properties. This allows for a compact, e.g. handheld, device which is capable of identifying or diagnosing or monitoring specifically selected diseases, such as Tuberculosis or Pneumonia, when the output data from the device is analysed. E.g. the device may comprise a processor arranged to perform such disease diagnosis or identification or monitoring, and wherein the communication module is then arranged to communicate the result of such diagnosis or identification of a disease, e.g. comprising a display and/or a loudspeaker and/or a wired or wireless interface to communicate such information to another device, e.g. a smartphone, a tablet or the like. In case of a handheld device, the handheld device itself may have a display, but alternatively or additionally, the device may communicate a gas analysis result for display on a patient monitor or a display on a ventilator device or the like.

The invention is based on the insight that space available for the necessary gas separators (e.g. GS columns) can be significantly reduced, since they each only need to be able to identify a specific range of molecules. Still, in combination, the plurality of gas separators can allow identification of specific biomarkers for identifying one or more selected diseases.

Compared to laboratory gas separators, e.g. using large GS columns, smaller GS columns separate the volatiles less well. However, in order to still be able to detect the molecules separately, multiple smaller GS columns can be used for separation. Suppose that molecule A of interest has two nearest neighbors, molecule B and C. If the first column is tuned to separate molecule A from molecule B, but not from molecule C, and the second column is tuned to separate molecule A from molecule C, but not from molecule B, it is still possible to deduce the individual abundances from molecule A, B and C.

The detector(s) may preferably at least provide a chromatography spectrum. Different molecules eluting on a different point in time. For the different gas separators, the molecules eluting, and this eluting time could be different. Further, the detector(s) may give additional information about the identified molecules, e.g. with respect to mass, or other, depending on the sensor type used in the detector(s).

The gas analysis device can be used to separate gaseous mixtures into multiple mixtures that can be further analysed. This can be used in a clinical setting, sampling breath samples directly from the side-stream of the tubing of a mechanical ventilator e.g. in intensive care units, or sampling from a bag containing a breath sample from patients that are able to breathe on their own. It can also be used in other applications where gases need to be analysed for the presence of specific components. It is to be understood that the device may be used as well to analyse VOCs in gases based on samples from skin, urine or feces. Further, the device may be used in general to analyse gas also for non-medical applications.

In the following, preferred embodiments or features of the first aspect will be described.

The first and second gas separators, or more than two gas separators, may comprise respective first and second gas chromatography (GC) columns. Especially, the at least one detector may comprises a mass spectrometry detector. Other detector types may be used, if preferred. Further, the flow path may split gas flow to allow more than two, e.g. three, four, or more, e.g. 5-10, or 10-20 GC columns to analyse the gas sample, wherein these GC columns are designed to have different molecule selectivity properties, so as to allow analysis with respect to molecules serving as biomarkers for one or more selected diseases. Especially, the first and second gas chromatography columns may have different molecule selectivity properties with respect to at least one of: chemical surface, diameter, surface thickness, and length.

The flow path may comprises a serial (i.e. sequential) flow path between the first and second gas separators. Preferably, the flow path comprises a parallel flow path between the first and second gas separators. In preferred embodiments, the flow path comprises more than two gas separators, wherein the gas flow is split to the more than two gas separators by means of a combination of at least one serial (i.e. sequential) flow path and at least one parallel flow path. Especially, the flow path may comprise three parallel flow paths each comprising one or more gas separator.

In preferred embodiments, the flow path comprises at least one serial flow path between a first set of a plurality of gas separators with different molecule selectivity properties, and wherein the flow path comprises at least one parallel flow path between a second set of a plurality of gas separators with different molecule selectivity properties.

The at least one detector may be arranged to generate respective first and second responses to outputs from the first and second gas separators being indicative of one of or a range of different molecules. Especially, the detector may be arranged to detect one specific molecule.

The at least one detector may comprise a first detector comprising a sensor arranged to generate a first response to an output from the first gas separators, and a second detector comprising a sensor arranged to generate a second response to an output from the second gas separator. I.e. separate detectors for each of the two gas separators. Alternatively, the at least one detector may comprise one common detector comprising a sensor arranged to generate respective first and second responses to outputs from the first and second gas separators. In embodiments with more than two gas separators, the device may comprise a plurality of detectors wherein some detectors are common for a plurality of gas separators, while other gas separators have separate detectors.

The flow path may comprise a plurality of parallel flow paths each comprising a serial flow path between a plurality of gas separators, and comprising respective detectors arranged to generate a response to an output from each of the plurality of gas separators in said respective parallel flow paths.

The flow path may comprise a plurality of parallel flow paths each comprising a serial flow path between a plurality of gas separators, and comprising one common detector arranged to generate a response to an output from each of the plurality of gas separators in said respective parallel flow paths separated over time. Thus, according to such detector configuration, each parallel flow path with a plurality of gas separators in serial configuration can be detected by one common detector, if detection is split into separate time slots.

The flow path may comprise a serial flow path between the first and second separators and a valve arranged in said serial flow path, wherein a first detector is arranged to generate a response to an output from the first separator, and wherein a control unit is arranged to open or close the valve in response to said response from the first detector, so as to selectively provide flow or no flow of gas to the second separator in response to an output from the first separator. Especially, a second detector may be arranged to generate a response to an output from the second separator.

The first and second separators may comprise different chemical coatings serving to favour respective different ranges of molecules. Here, it is possible to tailor the molecule selectivity for a set of a plurality of gas separators, e.g. 3-10 different gas separators, so as to allow detection of preselected molecules in the gas sample, e.g. with the purpose of identifying biomarkers relevant for one or more specific diseases.

The gas analysis device may comprise a processor programmed to identify preselected biomarker(s) in accordance with first and second responses, and to generate an output accordingly, e.g. an output indicative of identification of one or more diseases.

In preferred embodiments, a pre-concentrator is arranged in the flow path upstream of the gas separators, so as to increase concentration of molecules of interest. Further, a moisture removal filter may be included, e.g. if the gas analysis device is to be used for breath air directly from a person or animal.

The communication module may comprise a wired or wireless interface for communicating a result of the gas analysis in various ways. E.g. the device may in addition or alternatively comprise a display or audio for communicating the gas analysis result. The gas analysis device may comprise a processor programmed to compute one or more likely diseases in response to identified molecules in the gas sample, and such one or more diseases may be communicated via the communication module. The communication module may be arranged to communicate data indicative of a value related to an amount of a compound in related to a specific disease. Alternatively or additionally, the communication module may be arranged to communicate identified molecules in the gas sample, thus allowing external further analysis. The communication module may communicate result of gas analysis in the form of molecule abundance or disease offs to a connected platform, e.g. to a cloud based platform. The gas analysis device may be arranged to perform an analysis in response to responses from the detectors included in the device, e.g. by comparing measured abundances of one or more marker molecule with a pre-stored value(s), and based thereon, the communication module may be arranged to communicate data indicative of a chance on certain disease, e.g. by means of a percentage or by means of a binary or trinary decision output ("traffic light").

In a second aspect, the invention provides a handheld breath analysis device comprising a gas analysis device according to the first aspect, wherein the gas inlet is arranged to receive exhaled breath from a subject, and wherein the flow path, the at least one detector, and the communication module are arranged within one common casing.

The gas inlet may comprise a mouthpiece arranged on an exterior part of the casing, so as to allow the subject, a person or an animal, to directly breathe into the mouthpiece and thus provide a gas sample to be analysed. Other tube fittings may be used for connection to receive breathed air from a mechanical ventilator (in intensive care units or OR) to which the subject is connected. Still further, the gas inlet of the device may be arranged for mounting of a gas bag with the gas sample to be analyzed.

In a third aspect, the invention provides use of a gas analysis device according to the first aspect for analysis of a sample of exhaled breath from a subject.

In a fourth aspect, the invention provides a method for analysis of breath exhaled from a subject, the method comprising receiving a sample of exhaled breath obtained from the subject, guiding said sample in a flow path to at least first and second gas separators with respective first and second molecule selectivity properties, wherein the first and second molecule selectivity properties are different, detecting respective first and second responses to outputs from the first and second gas separators, and generating output data in response to said first and second responses.

In general, it is appreciated that the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
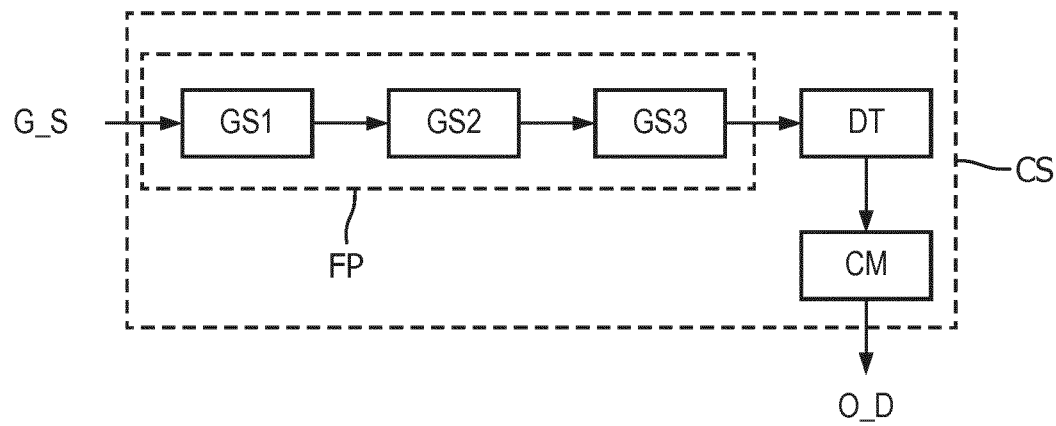
FIG. 1 illustrates in schematic form a gas analysis embodiment.

FIG. 1 shows in schematic form a handheld gas analysis device with a casing CS having a gas inlet arranged to receive a gas sample G_S in the form of a sample of breath exhaled, or VOCs from other sources, e.g. skin, uring, feces etc. from an animal or a person. The casing CS houses a flow path FP connected to the gas inlet so as to guide the gas sample to a set of three gas separators GS1, GS2, GS3 in a serial flow path connection. In a preferred embodiment, the gas separators GS2, GS2, GS3 are implemented as Gas chromatography Columns (GCs) with respective different molecule selectivity properties, e.g. with different chemical coatings, and/or other physical or chemical properties serving to allow detection of a specific range of molecules. The casing CS further houses one detector DT common for all three gas separators GS1, GS2, GS3 comprises a sensor arranged to detect outputs from the gas separators GS1, GS2, GS3, and to generate respective first, second, and third responses to outputs from the respective gas separators GS1, GS2, GS3 in response to their outputs. The detector DT may be such as a mass spectrometry type detector, however a number of other detector may be used, if preferred, e.g. metal oxide sensors, electrochemical sensors, plasma emission detectors (PEDs), thermal conductivity detectors (TCDs).

The casing CS further houses a communication module CM, e.g. for wireless radio frequency, e.g. wi-fi, communication of output data O_D indicative of the responses from the detector DT, so as to allow an external device, e.g. a computer or a smart phone or the like, to receive the result of the gas analysis performed on the gas sample. The handheld device may also comprise a processor arranged to receive the responses from the detector DT so as to calculate if one or a set of specific molecules are present in the gas sample, and wherein this result is then communicated by the communication module CM, e.g. comprising a display visible on the surface of the casing CS.

Figure 2:
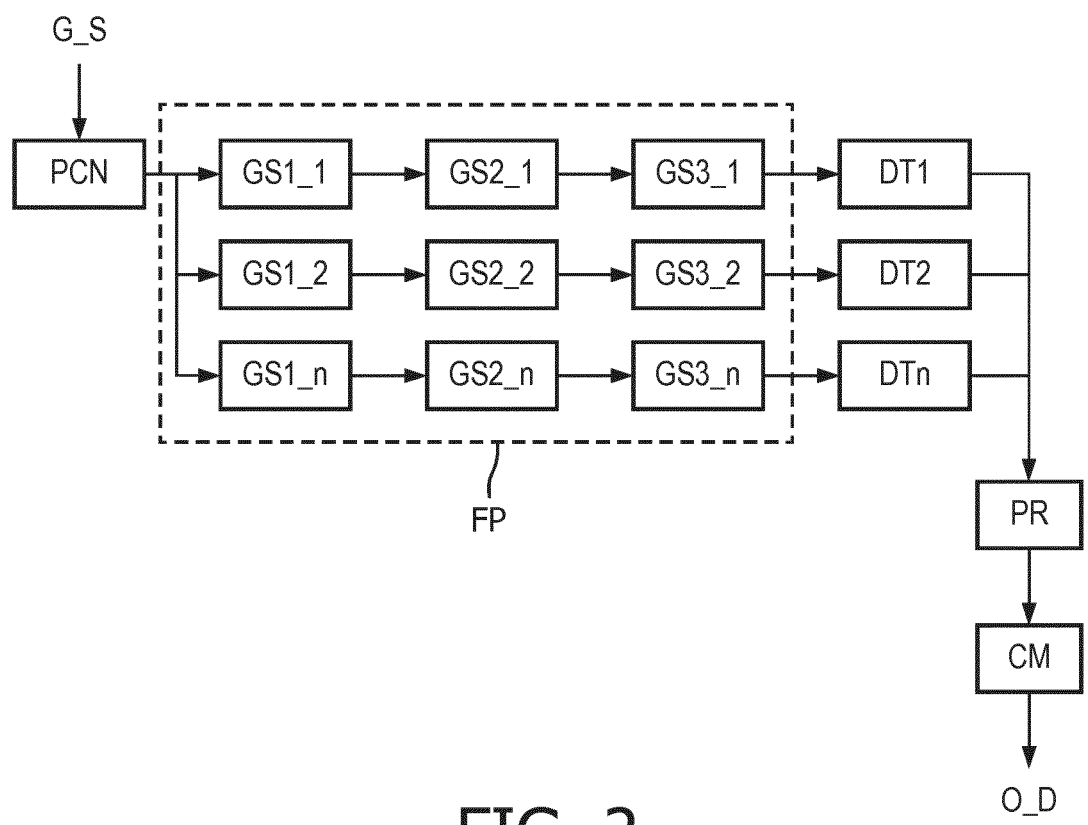
FIG. 2 illustrates another embodiment with parallel branches of a plurality of gas separators with one detector for each branch.

FIG. 2 illustrates in a schematic representation an embodiment with a flow path FP having parallel branches each having a plurality of gas separators GS1_1 to GS3_n connected in a serial path. As seen, three parallel connections each with a serial connection of three gas separators are seen, however 'n' indicates that the gas analysis device may in general comprise more than three parallel branches, and each branch may comprise more than three gas separators in serial connection.

The gas inlet in this embodiment, is connected to a pre concentrator PCN arranged to so as to increase concentration of molecules of interest prior to the gas sample G_S is guided to the gas separators GS1_1 to GS3_n. Especially, the coatings of the gas separators GS1_1 to GS3_n may be tuned in such a way that they favour a specific range of molecules, e.g. in the form of GCs with respective chemical/physical properties. At the end, the output of each series of gas separators is measured by separate detectors DT1, DT2, DT3. The combination of the specific responses of the sensors of the detectors DT1, DT2, DT3 combined with the separation of the VOCs will provide the input to filter the relevant analysis data for the disease or illness that needs to be diagnosed. Such processing may be performed by a processor PR included in the gas analysis device, and the final result from the gas analysis is then communicated as output data O_D from the communication module CM.

Figure 3:
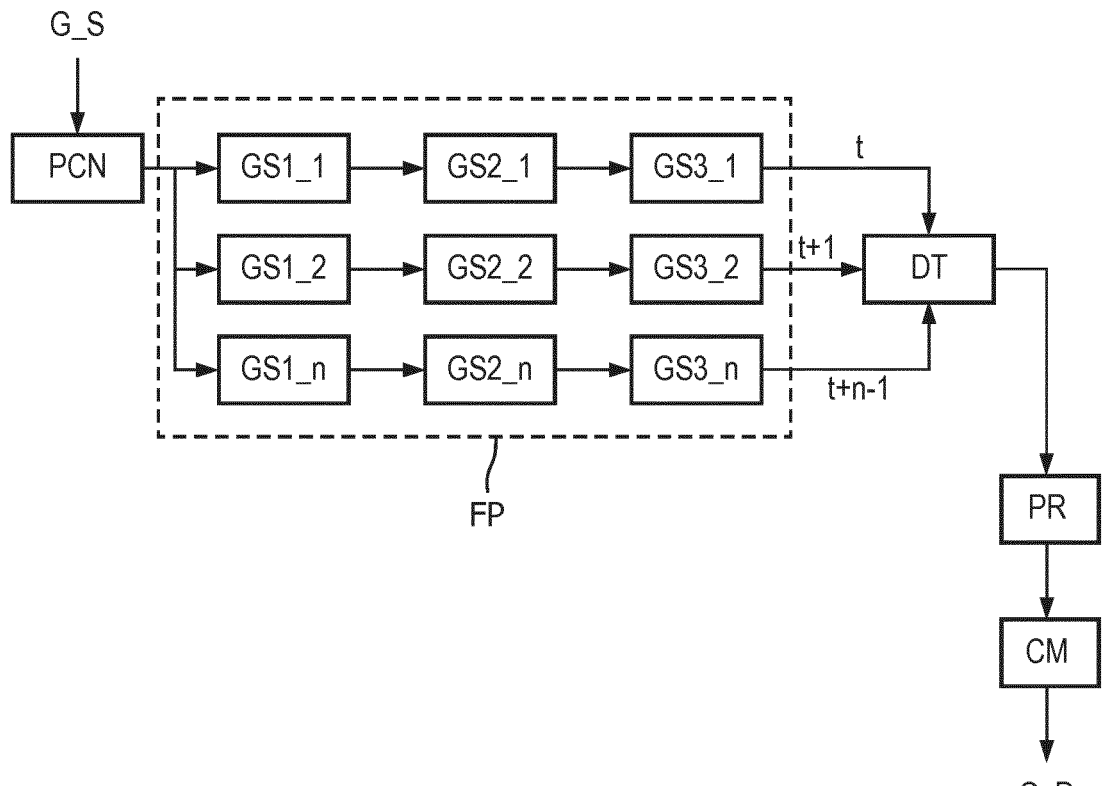
FIG. 3 illustrates yet another embodiment with parallel branches of a plurality of gas separators with one common detector for all of the parallel branches.

FIG. 3 illustrates an alternative version of the embodiment of FIG. 2, where the different is that the gas separators GS1_1 to GS3_n are connected to one common detector DT, which detects responses from the single gas separators GS1_1 to GS3_n separated over time, namely detected to times t, t+1, t+n−1, i.e. temporally separate for each of the parallel branches of gas separators. As an alternative to the shown one pre concentrator PCN, each parallel stream may have its own dedicated pre concentrator. This will allow (1) tuning the properties of the pre concentrator to the respective gas separators (e.g. columns) in the parallel branch, and (2) to sequentially releasing the VOCs adsorbed in the pre concentrator by thermal desorption. Sequential thermal desorption facilitates switching of the detector DT between the different flow paths, without missing any compounds.

Figure 4:
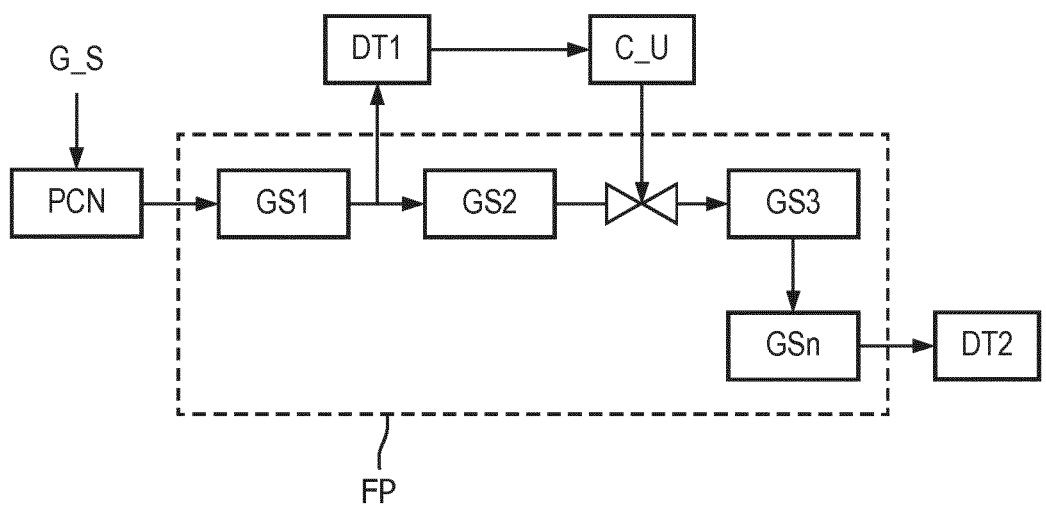
FIG. 4 illustrates an embodiment with an intermediate detector serving to control a valve, thereby allowing stopping of gas flow in case of harmful material which may harm downstream gas separators in the flow path.

FIG. 4 illustrates an embodiment with a valve controlled by a control unit C_U. The use of multiple gas separators, e.g. GCs, with different properties increases the selectivity of the full system. The coating of some of the GCs is preferably chosen such that the targeted biomarkers are optimally separated from the rest of the compounds present. However, the rest of the compounds may include aggressive molecules which can potentially damage the sensitive coating of the GCs. Therefore, in the embodiment of FIG. 4, the gas sample G_S, e.g. exhaled breath, is preconcentrated in the preconcentrator PCN. Subsequently, the gas flow is channeled through a first gas separator GS1, and the outcome of this gas separator GS1 is monitored by an intermediate detector DT1. Based on the outcome of the intermediate detector DT1 (which includes retention time, ion intensity, and possibly mass spectra as well), a control unit C_U closes or opens a valve in the flow path between gas separators GS2 and GS3. Thus, the control unit (C_U) is arranged to open or close the valve in response to said response from the first detector (DT1), so as to selectively provide flow or no flow of gas to the second separator (GS3) in response to an output from the first separator (GS1). Hereby, it can be ensured that only the interesting part of the chromatogram is fed into the sensitive gas separators GS3 to GSn. All other compounds are blocked and/or vented outwards. This prolongs the lifetime of the sensitive gas separators GS3 and further. The control unit C_U may calculate a decision regarding closing or opening the valve while the gas travels through separator GS2. A separate detector DT2 is arranged downstream of the valve and being arranged to detect outputs from gas separators GS2, GS3 and GSn.

The controllable valve concept described above and shown in FIG. 4 may be applied for other reasons than due to aggressive molecules. In general, one or more valves may be controlled by an initial first analysis of the sample using a first gas separator in the flow path. Based on this initial first column and detection, e.g. it can be analysed and based on the result it can be determined if the applied gas sample originates e.g. from breath or from urine. In case the gas sample is determined to originate from breath, the gas sample can be guided via the valve to one path A via one or more gas separators, and if it is determed to originate from urine, the valve may be controlled to guide the gas sample to another path B etc.

It is understood that the principle with a valve in the flow path can be extended or combined by more parallel and/or serial gas separator streams as shown in the embodiments of FIGS. 1-3.

Figure 5:
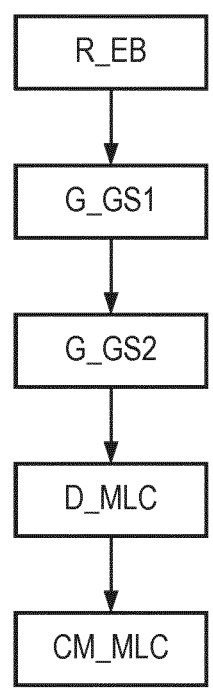
FIG. 5 illustrates a method embodiment.

FIG. 5 illustrates steps of an embodiment of a method for analysis of breath exhaled from a subject. The method comprising receiving a sample R_EB of exhaled breath obtained from the subject, e.g. in the form of a gas bag with exhaled breath obtained from the subject. The method further comprises guiding said sample in a flow path to at first gas separator G_GS1 and guiding the gas sample to a second gas separator G_GS2. The first and second gas separators are designed to have respective first and second molecule selectivity properties, wherein the first and second molecule selectivity properties are different. Next step is detecting respective first and second responses D_MLC to outputs from the first and second gas separators, and preferably to determine the presence or not of one or more preselected molecules in accordance with the first and second responses. Finally, an output is generated and communicated CM_MLC in response to said determining of molecule(s).

It is understood that the method may comprise diagnosing a disease based on a result of analysing exhaled breath from a subject according to the gas analysis method. The method may further comprise initiating a specific therapy, e.g. a medical treatment of Tuberculosis. Further, breath VOC analysis may be used for monitoring/analysis of lung cancer, breast cancer, other types of cancer, or respiratory infections. Also, breath analysis may be applicable for monitoring diseases such as asthma and Chronic Obstructive Pulmonary Disease (COPD) e.g. response to treatment, exacerbation monitoring. Furthermore, breath analysis may further be applied for monitoring glucose level in diabetes. Still further, an application example may be monitoring for sepsis and necrotizing enterocolitis (NEC) from VOC analysis based on gas analysis based on feces in neonates.

To sum up, the invention provides A gas analysis device suited for e.g. medical analysis of exhaled breath from a subject. A gas inlet receives a gas sample to a flow path for guiding the gas sample to two or more gas separators, e.g. gas chromatography columns, with respective molecule selectivity properties which are different. One or more detectors, each with a sensor, are arranged to generate respective responses to outputs from the two or more gas separators. A communication module generate output data in response to the respective responses from the one or more detectors, e.g. data indicative of molecules in the gas sample. E.g. a flow path with several parallel paths each comprising one or more gas separator may be used.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:
1. A gas analysis device, comprising:
a gas inlet arranged to receive a gas sample;
a flow path connected to the gas inlet and being arranged to guide the gas sample to first and second gas separators with respective first and second molecule selectivity properties, wherein the first and second molecule selectivity properties are different;
first and second detectors, each comprising a sensor arranged to generate respective first and second responses to outputs from the first and second gas separators;

a third gas separator disposed in a serial flow path with the first and second gas separators;
a valve arranged in the serial flow path between the second and third gas separators;
a transceiver arranged to generate output data in response to the first and second responses from the first and second detectors, wherein the first detector is arranged to generate a response to an output from the first gas separator; and
a controller arranged to open or close the valve in response to the response from the first detector, so as to selectively provide flow or no flow of gas to the third gas separator in response to an output from the first gas separator.

2. The gas analysis device according to claim 1, wherein the first and second gas separators comprise different molecular selectivity properties so as to favour respective different ranges of molecules.

3. The gas analysis device according to claim 1, wherein the first and second gas separators comprise respective first and second gas chromatography columns.

4. The gas analysis device according to claim 3, wherein the first and second gas chromatography columns have different molecule selectivity properties with respect to at least one of: chemical surface, diameter, surface thickness, and length.

5. The gas analysis device according to claim 1, comprising a first detector comprising a sensor arranged to generate a first response to an output from the first gas separator, and a second detector comprising a sensor arranged to generate a second response to an output from the third gas separator.

6. The gas analysis device according to claim 1, comprising one common detector comprising a sensor arranged to generate respective first and second responses to outputs from the first and second gas separators.

7. The gas analysis device according to claim 1, wherein the flow path comprises a plurality of parallel flow paths each comprising a serial flow path between a plurality of gas separators, and comprising respective detectors arranged to generate a response to an output from each of the plurality of gas separators in the respective parallel flow paths.

8. The gas analysis device according to claim 1, wherein the flow path comprises a plurality of parallel flow paths each comprising a serial flow path between a plurality of gas separators, and comprising one common detector arranged to generate a response to an output from each of the plurality of gas separators in the respective parallel flow paths separated over time (t, t+1, t+n−1).

9. A handheld breath analysis device comprising a gas analysis device according to claim 1, wherein the gas inlet is arranged to receive exhaled breath from a subject, and wherein the flow path, the first and second detectors, and the transceiver are arranged within one common casing.

10. A gas analysis device, comprising:
a gas inlet arranged to receive a gas sample;
a flow path connected to the gas inlet and being arranged to guide the gas sample to at least first and second gas separators with respective first and second molecule selectivity properties, wherein the first and second molecule selectivity properties are different;
first and second detectors, each comprising a sensor arranged to generate respective first and second responses to outputs from the first and second gas separators;
a third gas separator disposed in a serial flow path with the first and gas second separators;
a valve arranged in the serial flow path between the second and third gas separators;
a transceiver arranged to generate output data in response to the first and second responses from the first and second detectors, wherein the first detector is arranged to generate a response to an output from the first gas separator;
a controller arranged to open or close the valve in response to the response from the first detector, so as to selectively provide flow or no flow of gas to the third gas separator in response to the output from the first gas separator;
a processor; and
a non-transitory computer-readable medium that stores instructions, which when executed by the processor cause the processor to identify a preselected biomarker in accordance with first and second responses.

11. The gas analysis device according to claim 10, wherein the preselected biomarker are relevant for one or more specific diseases.

12. The gas analysis device according to claim 10, wherein the first and second gas separators comprise different molecular selectivity properties so as to favor respective different ranges of molecules.

13. The gas analysis device according to claim 10, wherein the first and second gas separators comprise respective first and second gas chromatography columns.

14. The gas analysis device according to claim 13, wherein the first and second gas chromatography columns have different molecule selectivity properties with respect to at least one of: chemical surface, diameter, surface thickness, and length.

* * * * *